(12) United States Patent
Hoshi et al.

(10) Patent No.: US 12,736,513 B2
(45) Date of Patent: Sep. 15, 2026

(54) METHOD AND DEVICE FOR ANALYZING IONIC COMPONENTS IN ULTRAPURE WATER

(71) Applicants: KURITA WATER INDUSTRIES LTD., Tokyo (JP); NATIONAL UNIVERSITY CORPORATION KUMAMOTO UNIVERSITY, Kumamoto (JP)

(72) Inventors: Shigeyuki Hoshi, Tokyo (JP); Toshimasa Katou, Tokyo (JP); Takeo Fukui, Tokyo (JP); Shin-ichi Ohira, Kumamoto (JP); Kei Toda, Kumamoto (JP)

(73) Assignees: KURITA WATER INDUSTRIES LTD., Tokyo (JP); NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 281 days.

(21) Appl. No.: 18/694,427

(22) PCT Filed: Sep. 7, 2022

(86) PCT No.: PCT/JP2022/033586
§ 371 (c)(1),
(2) Date: Mar. 22, 2024

(87) PCT Pub. No.: WO2023/053876
PCT Pub. Date: Apr. 6, 2023

(65) Prior Publication Data

US 2024/0385164 A1 Nov. 21, 2024

(30) Foreign Application Priority Data

Sep. 28, 2021 (JP) ................................ 2021-158070

(51) Int. Cl.
*G01N 33/18* (2006.01)
*G01N 1/40* (2006.01)

(52) U.S. Cl.
CPC ......... *G01N 33/182* (2013.01); *G01N 1/4005* (2013.01); *G01N 2001/4016* (2013.01); *G01N 2001/4038* (2013.01)

(58) Field of Classification Search
CPC ............... G01N 33/182; G01N 1/4005; G01N 2001/4016; G01N 2001/4038;
(Continued)

(56) References Cited

U.S. PATENT DOCUMENTS

| | | | | |
|---|---|---|---|---|
| 6,686,751 B1 * | 2/2004 | Saito | G01N 33/182 | 204/263 |
| 6,911,152 B2 * | 6/2005 | Kim | G01N 33/182 | 210/85 |

(Continued)

FOREIGN PATENT DOCUMENTS

| | | |
|---|---|---|
| CN | 102854082 | 1/2013 |
| JP | H05220479 | 8/1993 |

(Continued)

OTHER PUBLICATIONS

"Office Action of Taiwan Counterpart Application", issued on Dec. 29, 2025, with English translation thereof, pp. 1-10.

(Continued)

*Primary Examiner* — Freddie Kirkland, III
(74) *Attorney, Agent, or Firm* — JCIPRNET

(57) ABSTRACT

Provided is a method which is for analyzing ionic components in pure water and in which sample ultrapure water is concentrated and analyzed by an analysis means, the method being characterized in that the sample ultrapure water is concentrated by means of an electrodialyzer. The electrodialyzer is a second electrodialyzer (20) in which sample (Continued)

ultrapure water is passed through a first generation chamber (27), high-purity nitric acid aqueous solution is passed through a second generation chamber (28), and concentrated water for analysis is extracted from the second generation chamber (28). The high-purity nitric acid aqueous solution passing through the second generation chamber (28) is generated by dialyzing a potassium nitrate aqueous solution by a first electrodialyzer (10).

7 Claims, 2 Drawing Sheets

(58) Field of Classification Search
CPC ........ G01N 33/18; B01D 61/44; B01D 61/46; B01D 61/445; C02F 1/469; C02F 1/4693
See application file for complete search history.

(56) References Cited

U.S. PATENT DOCUMENTS

| | | | | |
|---|---|---|---|---|
| 8,871,073 | B2 * | 10/2014 | Hasegawa | B01D 61/48 204/632 |
| 2003/0080063 | A1 * | 5/2003 | Kim | B01J 47/04 210/660 |
| 2004/0048389 | A1 * | 3/2004 | Liu | B01D 69/02 436/161 |
| 2006/0231406 | A1 * | 10/2006 | Freydina | B01D 61/54 204/632 |
| 2009/0152117 | A1 * | 6/2009 | Akahori | C02F 1/4693 204/630 |
| 2016/0220958 | A1 * | 8/2016 | Fukui | B01D 61/147 |
| 2022/0242757 | A1 * | 8/2022 | Ozawa | C02F 1/46109 |

FOREIGN PATENT DOCUMENTS

| | | |
|---|---|---|
| JP | H06130007 | 5/1994 |
| JP | H10232226 | 9/1998 |
| JP | 2001153855 | 6/2001 |
| JP | 2002168845 | 6/2002 |
| JP | 2007313421 | 12/2007 |
| JP | 2021084045 | 6/2021 |

OTHER PUBLICATIONS

"International Search Report (Form PCT/ISA/210) of PCT/JP2022/033586", mailed on Nov. 22, 2022, with English translation thereof, pp. 1-4.

"Notice of Reasons for Refusal of Japan Counterpart Application", issued on Nov. 15, 2022, with English translation thereof, p. 1-p. 4.

* cited by examiner

METHOD AND DEVICE FOR ANALYZING IONIC COMPONENTS IN ULTRAPURE WATER

CROSS-REFERENCE TO RELATED APPLICATION

This application is a 371 application of the International PCT application serial no. PCT/JP2022/033586, filed on Sep. 7, 2022, which claims the priority benefit of Japan Patent Application No. 2021-158070, filed on Sep. 28, 2021. The entirety of each of the above-mentioned patent applications is hereby incorporated by reference herein and made a part of this specification.

TECHNICAL FIELD

The present invention relates to a method and a device for analyzing ionic components in ultrapure water.

RELATED ART

An evaporative concentration method is often used in analysis of a trace amount of dissolved ions in ultrapure water. For example, in the case of metal cations, ultrapure water is concentrated by a rotary evaporator made of quartz, and the metal cations are detected by an electrically heated atomic absorption spectrometer or an inductively coupled plasma mass spectrometer (JIS K0553). However, this method has risks such as contamination caused by manually performing a complex operation or scattering of the metal cations along with vaporization of a solvent during evaporation.

Patent Document 1 describes the following method. Sample ultrapure water is sprayed into clean air, the resulting droplets are evaporated with clean hot air, and dried particles consisting of evaporation residue are collected using a membrane filter for spectroscopic analysis.

Patent Document 2 describes the following method. Ultrapure water is passed through a porous membrane having an ion exchange group, and impurities captured by the porous membrane are analyzed by a surface analyzer.

An example of Patent Document 3 describes the following method. Ultrapure water is passed through an ion adsorption membrane to adsorb metals in the ultrapure water, followed by elution with nitric acid, and the eluate is subjected to ICP-MS measurement.

Patent Document 4 describes a method for analyzing an extremely trace amount of ions in ultrapure water, which includes a process for passing the ultrapure water through a concentration column for concentration.

However, the methods described in Patent Documents 1 to 4 also have drawbacks such as requiring a lot of labor or a long time.

PRIOR-ART DOCUMENTS

Patent Documents

Patent Document 1: Japanese Patent Laid-open No. H6-130007

Patent Document 2: Japanese Patent Laid-open No. 2001-153855

Patent Document 3: Japanese Patent Laid-open No. 2021-84045

Patent Document 4: Japanese Patent Laid-open No. 2002-168845

SUMMARY OF THE INVENTION

Problems to be Solved by the Invention

The present invention aims to provide a method and a device for analyzing ionic components in ultrapure water, in which conventional problems such as an increase in blank due to contamination from chemicals or operation, and a delay in water quality diagnosis due to time-consuming analysis can be solved, blank can be reduced without contamination, and concentration and analysis can be performed with high sensitivity and on time.

Means for Solving the Problems

A method for analyzing ionic components in ultrapure water of the present invention is a method for analyzing ionic components in ultrapure water in which sample ultrapure water is concentrated and analyzed by an analysis part, the method being characterized in that the sample ultrapure water is concentrated by an electrodialyzer.

A device for analyzing ion components in ultrapure water of the present invention includes an electrodialyzer that concentrates sample ultrapure water, and an analysis part that measures an ion concentration in concentrated water concentrated by the electrodialyzer.

In one aspect of the present invention, the electrodialyzer is a second electrodialyzer that includes a first anion exchange membrane, a dialysis membrane, and a second anion exchange membrane arranged in this order between an anode and a cathode, and that includes an anode chamber, a first generation chamber, a second generation chamber, and a cathode chamber arranged in this order from the anode to the cathode. Sample ultrapure water is passed through the first generation chamber. A nitric acid aqueous solution is passed through the anode chamber and the cathode chamber. A high-purity nitric acid aqueous solution is passed through the second generation chamber, the high-purity nitric acid aqueous solution being generated by transmitting $NO_3^-$ ions through an anion exchange membrane by a dialysis treatment and causing the $NO_3^-$ ions to move in ultrapure water. Concentrated water from the second generation chamber is analyzed by the analysis part.

In one aspect of the present invention, the high-purity nitric acid aqueous solution that is passed through the second generation chamber of the second electrodialyzer is generated by dialyzing a nitrate aqueous solution by a first electrodialyzer.

In one aspect of the present invention, the first electrodialyzer is an electrodialyzer that includes a bipolar exchange membrane and an anion exchange membrane arranged in this order between an anode and a cathode, and that includes an anode chamber, a nitric acid generation chamber, and a cathode chamber arranged in this order from the anode to the cathode. Ultrapure water is passed through the anode chamber and the nitric acid generation chamber. A nitrate aqueous solution is passed through the cathode chamber. The high-purity nitric acid aqueous solution is extracted from the nitric acid generation chamber.

In one aspect of the present invention, the nitrate includes potassium nitrate, sodium nitrate, or lithium nitrate.

Effects of the Invention

In the present invention, dissolved ions in the sample ultrapure water are continuously concentrated by the electrodialyzer and directly introduced into a measuring instrument. By handling a concentrated liquid obtained from the sample ultrapure water in a closed flow system, contamination from a measurement environment may be prevented.

In one aspect of the present invention, by applying improvements to device structure, membrane selection, how to create a solution channel or the like in the electrodialyzer (ion extraction device) that realizes real-time concentration, the influence of contamination within the device may be eliminated.

According to one aspect of the present invention, by continuously concentrating the dissolved ions in the sample ultrapure water and directly introducing them into the measuring instrument, highly sensitive continuous monitoring can also be achieved. Since the concentration process is carried out in a closed system within a flow device, there is no contamination from the surrounding environment. Since the operation is unattended and fully automatic, there is no human contamination. Furthermore, since fine particles in the sample ultrapure water cannot be transmitted through the membrane and are not extracted, removal and concentration of impurities can be achieved at the same time, and sensitivity and accuracy can be improved.

In one aspect of the present invention, as a device that generates an acid used for ion extraction, the first electrodialyzer (acid solution generator) that is able to stably supply acid of high purity and arbitrary concentration is used. In preparation of a standard solution, to prevent reduction in accuracy due to a difference in elution level from a container, while blank sample water is placed in the container and the amount of reduction is monitored in mass thereof, a standard solution of a target component is added as appropriate. When an extremely low concentration is continuously measured, since it is desirable to measure a blank sample on a regular basis, in one aspect of the present invention, a blank sample is refined and supplied in line by reusing a sample solution after measurement.

According to the present invention, as described above, since the concentration of metal ions or the like in ultrapure water can be continuously concentrated, on-site on-line analysis at a semiconductor factory or the like becomes possible. According to one aspect of the present invention, it is possible to supply high-purity blank water or chemicals. It is also possible to reduce blank and save space.

According to the present invention, it is possible to quickly diagnose the quality of ultrapure water. Hence, by quickly determining the water quality at start-up after maintenance of an ultrapure water production device, cost losses at a factory can be prevented. Furthermore, in the future, it will be possible to support fully automated and unmanned factories due to AI and IoT.

Conventionally, a sample solution collected on site is taken back to a clean room and then subjected to a series of operations. According to the present invention, it is possible to concentrate the sample solution in line and collect the sample solution for each fraction at the same time as collecting the sample solution on site. In this way, transportation cost can be reduced and measurement can be performed with high temporal resolution. The present invention describes a universal method with respect to dissolved ions, in which continuous monitoring on site with much higher sensitivity than conventionally is possible if an in-line sensor is provided in a measuring instrument in a subsequent stage. In one aspect of the present invention, an acid is generated by an in-line generator to prepare blank water from sample ultrapure water. Accordingly, not only dissolved ions can be concentrated, but accurate measurement can be performed at extremely low concentrations.

DESCRIPTION OF THE EMBODIMENTS

Figure 1:
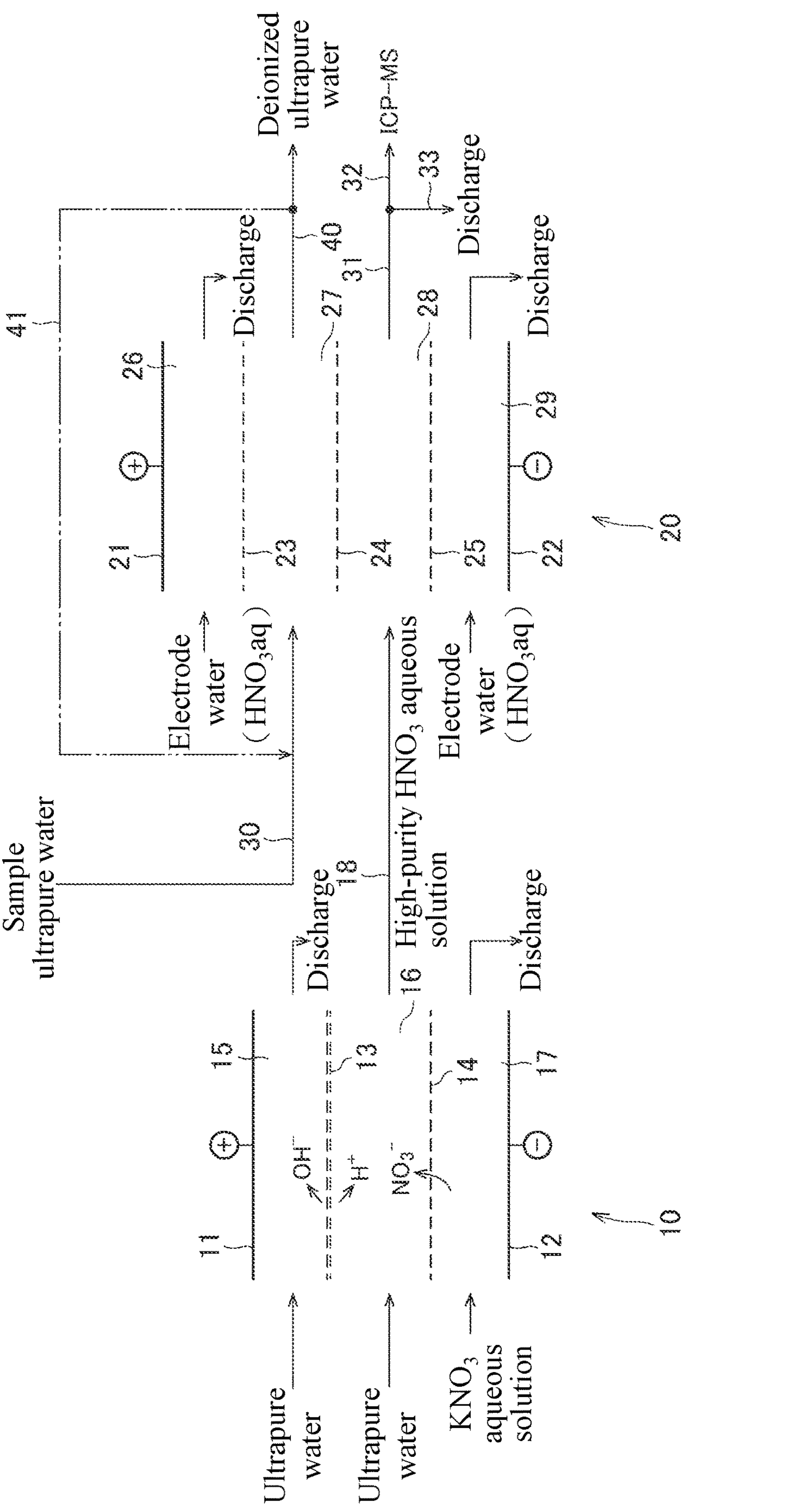
FIG. 1 describes a method and a device for analyzing ionic components in ultrapure water according to an embodiment.

Hereinafter, a method and a device for analyzing ionic components in ultrapure water according to an embodiment will be described with reference to FIG. 1. In the present embodiment, a metal ion concentration in ultrapure water is 10 ng/L or less. However, the disclosure is not limited thereto.

In the method and the device for analyzing ionic components in ultrapure water, a first electrodialyzer 10 and a second electrodialyzer 20 are used.

In the first electrodialyzer 10, a bipolar membrane 13 and an anion exchange membrane 14 are arranged between an anode 11 and a cathode 12. An anode chamber 15 is formed between the anode 11 and the bipolar membrane 13. A nitric acid generation chamber 16 for high-purity nitric acid aqueous solution is formed between the bipolar membrane 13 and the anion exchange membrane 14. A cathode chamber 17 is formed between the anion exchange membrane 14 and the cathode 12.

A bipolar membrane is a composite membrane having a structure in which a cation exchange membrane and an anion exchange membrane are superimposed. Bipolar membrane has conventionally been widely used as a diaphragm in electrolysis of water, or as a separation membrane during regeneration of acids and alkalis from an aqueous solution of a salt which is a product of neutralization of acids and alkalis, or the like. In the bipolar membrane 13, since water dissociation occurs by application of a voltage equal to or higher than a theoretical water electrolysis voltage (0.83 V), a current flows.

As described above, the bipolar membrane 13 has a structure in which a cation exchange membrane and an anion exchange membrane are superimposed. Hence, in the first electrodialyzer 10, even in a state in which a voltage is applied between the anode 11 and the cathode 12, ions in the anode chamber 15 and the nitric acid generation chamber 16 are not transmitted through the bipolar membrane 13.

In the state in which a voltage is applied between the anode 11 and the cathode 12, when ultrapure water is supplied to the anode chamber 15 and the nitric acid generation chamber 16, and $KNO_3$ aqueous solution is supplied to the cathode chamber 17, $NO_3^-$ ions in the cathode chamber 17 are transmitted through the anion exchange membrane 14 and move to the nitric acid generation chamber 16. Cations in the cathode chamber 17 are not transmitted through the anion exchange membrane 14 and thus do not move to the nitric acid generation chamber 16. Due to the action of the bipolar membrane 13, water is dissociated and $H^+$ is generated. In this way, high-purity nitric acid aqueous solution is continuously generated by the nitric acid generation chamber 16, extracted via an extraction line 18, and conveyed to a second generation chamber 28 of the second electrodialyzer 20. The above $KNO_3$ aqueous solution has a concentration of about 1 mmol/L to 10 mmol/L. However, the disclosure is not limited thereto.

In the second electrodialyzer 20, an anion exchange membrane 23, a dialysis membrane 24, and an anion exchange membrane 25 are arranged in this order between an anode 21 and a cathode 22. An anode chamber 26 is formed between the anode 21 and the anion exchange membrane 23. A first generation chamber 27 for generating deionized ultrapure water is formed between the anion exchange membrane 23 and the diagnosis membrane 24. A second generation chamber 28 for generating concentrated water is formed between the dialysis membrane 24 and the anion exchange membrane 25. A cathode chamber 29 is formed between the anion exchange membrane 25 and the cathode 22. A diagnosis membrane made of sufficiently cleaned regenerated cellulose or cellulose ester can be used for the diagnosis membrane. The dialysis membrane used has a molecular weight cut-off of suitably 6,000 to 10,000. However, the disclosure is not limited thereto.

In a state in which a voltage is applied between the anode 21 and the cathode 22, electrode water made of nitric acid aqueous solution is supplied to each of the anode chamber 26 and the cathode chamber 29, sample ultrapure water is supplied to the first generation chamber 27 via a sample water line 30, and high-purity $HNO_3$ aqueous solution from the first electrodialyzer 10 is supplied to the second generation chamber 28. The nitric acid aqueous solution supplied to the anode chamber 26 and the cathode chamber 29 has a concentration of about 10 mmol/L to 30 mmol/L. However, the disclosure is not limited thereto.

Accordingly, cations in the sample ultrapure water flowing in the first generation chamber 27 are transmitted through the diagnosis membrane 24 and move to the second generation chamber 28. $NO_3^-$ in the nitric acid aqueous solution flowing in the cathode chamber 29 is transmitted through the anion exchange membrane 25 and moves to the second generation chamber 28. Accordingly, concentrated water containing the cations that have moved from the sample ultrapure water and nitrate ions flows out from the second generation chamber 28. By adjusting the amount of sample ultrapure water supplied to the first generation chamber 27, the amount of high-purity nitric acid aqueous solution supplied to the second generation chamber 28, and the applied voltage, concentrated water having a higher cation concentration than the sample ultrapure water is generated by the second generation chamber 28.

By supplying this concentrated water to an analyzer such as ICP-MS via lines 31 and 32 for analysis, and dividing a measured value by a concentration ratio, the cation concentration in the sample ultrapure water can be determined with high accuracy.

Anions in the sample ultrapure water supplied to the first generation chamber 27 pass through the anion exchange membrane 23 and move to the anode chamber 26, and the cations move from the first generation chamber 27 to the second generation chamber 28 through the dialysis membrane 24. Accordingly, deionized ultrapure water of high purity (having a lower ion concentration than the sample ultrapure water) which has been highly deionized may be obtained from the first generation chamber 27. This deionized ultrapure water is extracted via a line 40 and can be used for blank water, cleaning water for an electrodialyzer, or the like.

In this embodiment, the second electrodialyzer 20 has a four-chamber structure including four chambers 26 to 29. As an electrodialyzer, there is one having a five-chamber structure in which a dialysis membrane (second dialysis membrane) is further arranged between the anion exchange membrane 23 and the dialysis membrane 24, and sample ultrapure water is supplied between the dialysis membrane 24 and the second dialysis membrane. This electrodialyzer having a five-chamber structure may be used in the case of separating, refining, and concentrating cations and anions at the same time. In the case of evaluating either cations or anions, it is desirable to use an electrodialyzer having a four-chamber structure. In the present system, since cations in ultrapure water are to be analyzed, an electrodialyzer having a four-chamber structure is used.

As described above, the cations in the sample ultrapure water are transmitted through the diagnosis membrane 24 from the first generation chamber 27 and move to the second generation chamber 28. By controlling a flow rate ratio and a current value of the first generation chamber 27 and the second generation chamber 28, a concentration rate is determined. By flowing $HNO_3$ solution as an isolator layer through the anode chamber 26 and the cathode chamber 29, entry of contaminants into sample water and concentrated water or deterioration of a membrane in contact with an electrode part due to high temperatures can be prevented, and voltage and current efficiency can be improved.

As described above, since deionized ultrapure water may be obtained from the first generation chamber 27, this deionized ultrapure water can be used as clean blank water, purge water, rinse water or the like. For example, by circulating and reusing the deionized ultrapure water as blank water via a line 41, the deionized ultrapure water can be used as blank water before a concentration operation of the second electrodialyzer 20, or can be used in line cleaning before and after concentration of each analysis sample when the samples are concentrated and analyzed.

In quantitative analysis of cations (metal ions) in the present system, a calibration relationship is determined in advance from a concentrated blank concentration (metal blank concentration when blank water is concentrated) using the second electrodialyzer 20 and a metal ion concentration in each target quantitative analysis range. To prevent on-site contamination, a metal standard solution is added to ultrapure water prepared in advance, and the amount added is gradually increased, thereby preparing aqueous solutions of known concentrations whose concentrations are different. When the metal standard solution is added, it is preferable to measure the weight of the ultrapure water to which the metal standard solution is added and detect the amount of the metal standard solution added. Accordingly, a calibration curve can be created and steady state performance of the second electrodialyzer 20 can be confirmed without preparing a standard solution bottle for each metal concentration. When a calibration curve is created or the like, necessary metal standard stock solution is added with respect to the weight of the reduced amount of the ultrapure water or the metal standard solution supplied to the second electrodialyzer 20. It is desirable to always install a metal standard solution bottle, a weight measuring instrument or the like in a locally clean environment, and to use, for example, a small-size $N_2$ gas box.

Preferred examples of each process and conditions of a method for analyzing cations (metal) using the present system are described below.

[(1) Start-Up Process]

Blank water (deionized ultrapure water) is supplied to the first generation chamber 27 via the line 41, high-purity $HNO_3$ aqueous solution generated by the first electrodialyzer 10 is supplied to the second generation chamber 28 via the line 18, $HNO_3$ aqueous solution is supplied to each of the anode chamber 26 and the cathode chamber 29, and the entire second electrodialyzer 20 is initially cleaned. During the initial cleaning, a voltage is moderately applied between the anode 21 and the cathode 22. Water flowing from the second generation chamber 28 is discharged via a drainage line 33. An ICP-MS introduction line 32 is flushed with high-purity $HNO_3$ aqueous solution that is separately prepared.

[(2) Calibration Curve Creation Process]

Blank water (deionized ultrapure water) or prepared ultrapure water to which a metal standard solution has been added is supplied to the first generation chamber 27, and high-purity $HNO_3$ aqueous solution from the first electrodialyzer 10 is supplied to the second generation chamber 28. $HNO_3$ aqueous solution is supplied to each of the anode chamber 26 and the cathode chamber 29. Firstly, a concentration blank value due to voltage application is determined using blank water, and then a calibration curve is created using the ultrapure water to which a metal standard solution has been added. At intervals when the concentration of the ultrapure water to which a metal standard solution has been added that is passed is changed, blank water from the first generation chamber 27 is circulated and supplied to the first generation chamber 27 through the line 41, a voltage is applied and initial cleaning is performed. At that time, the concentrated water from the second generation chamber 28 is discharged to the drainage line 33. During a measurement for creating a calibration curve, the concentrated water is introduced into ICP-MS for analysis.

[(3) Sample Concentration/Analysis Process]

Sample ultrapure water is supplied to the first generation chamber 27, and the high-purity $HNO_3$ aqueous solution from the first electrodialyzer 10 is supplied to the second generation chamber 28. $HNO_3$ aqueous solution is supplied to each of the anode chamber 26 and the cathode chamber 29. A voltage is applied between the anode 21 and the cathode 22, and the concentrated water from the second generation chamber 28 is introduced into ICP-M S via the lines 31 and 33 for on-line analysis. After measurement, the blank water from the first generation chamber 27 is circulated to the first generation chamber 27 via the line 41, and then sample ultrapure water is supplied again for second on-line analysis. A voltage may be applied between the anode and the cathode during blank water circulation, or a concentrated blank between measurement intervals of the sample ultrapure water can be subjected to ICP-M S analysis and a blank concentration may be confirmed.

[(4) Lowering Process]

Blank water (deionized ultrapure water) is supplied to the first generation chamber 27 via the line 41, and the high-purity $HNO_3$ aqueous solution from the first electrodialyzer 10 is supplied to the second generation chamber 28. $HNO_3$ aqueous solution is supplied to each of the anode chamber 26 and the cathode chamber 29. A voltage is applied between the anode and the cathode, and the inside of the second electrodialyzer 20 is subjected to initial cleaning. Cleaning wastewater is discharged via the drainage line 33. The ICP-MS introduction lines 31 and 32 are flushed with high-purity $HNO_3$ aqueous solution that is separately prepared.

After the initial cleaning, ultrapure water is supplied to the second generation chamber 28. Ultrapure water is also supplied to the anode chamber 26 and the cathode chamber 29. At this time, ultrapure water is passed through the chambers 15, 16, and 17 while the first electrodialyzer 10 is turned off. After all the chambers are cleaned in this way, water is stopped from being passed to each chamber, and a water-sealed state is achieved in advance.

EXAMPLES

Metal ion concentration in ultrapure water was measured using the following first electrodialyzer 10, second electrodialyzer 20, and ICP-M S under the following conditions.

Experimental Method

<First Electrodialyzer>

- Electrode area: 2 $cm^2$
- Bipolar membrane: Neocepta BP-1E, manufactured by ASTOM Corporation
- Anion exchange membrane: model number: DSVN, manufactured by AGC Engineering Co., Ltd.
- Spacing between anode and bipolar membrane: 0.1 mm
- Spacing between bipolar membrane and anion exchange membrane: 0.13 mm
- Spacing between anion exchange membrane and cathode: 0.13 mm
- Distance from inlet to outlet of each chamber: 40 mm <Second Electrodialyzer>

- Electrode area: 2 $cm^2$
- Dialysis membrane: SpectrPor cellulose ester dialysis tube (product code: 131276)
- Anion exchange membrane: model number: DSVN, manufactured by AGC Engineering Co., Ltd.
- Spacing between anode and anion exchange membrane: 0.1 mm
- Spacing between anion exchange membrane and dialysis membrane: 0.13 mm
- Spacing between dialysis membrane and anion exchange membrane: 0.13 mm
- Spacing between anion exchange membrane and cathode: 0.1 mm
- Distance from inlet to outlet of each chamber: 40 mm <Analyzer>

- ICP-MS: iCAP-RQ, manufactured by Thermo Scientific, measurement/KED mode
- Metal standard solution: ICP mixed standard solution H (20262-23), manufactured by Kanto Chemical <Water Passing and Operating Conditions During Device Startup/Flushing>

<<Second Electrodialyzer and ICP-MS>>

- Sample water: ultrapure water, 5 mL/min
- Water supply to second generation chamber 28: $HNO_3$ (1 mM), 0.1 mL/min
- Water supply to anode and cathode: $HNO_3$ (10 mM), 2 mL/min
- ICP-M S introduction water: $HNO_3$ (1 mM), 0.1 mL/min
  - Circulate the water flowing out from the first generation chamber 27 to the inlet of the first generation chamber 27
  - Discard the concentrated water flowing out from the second generation chamber 28

<<First Electrodialyzer>>

Water supply to anode chamber: ultrapure water, 2 mL/min

Water supply to cathode chamber: $KNO_3$ (10 mM), 2 mL/min

Water supply to nitric acid generation chamber 16: ultrapure water, 0.1 mL/min <Water Passing and Operating Conditions During Concentration and Analysis Using Metal Standard Solution>

<<Second Electrodialyzer and ICP-MS>>

Sample water: ultrapure water, 5 mL/min

Water supply to second generation chamber 28: $HNO_3$ (1 mM), 0.1 mL/min

Water supply to anode chamber and cathode chamber: $HNO_3$ (10 mM), 2 mL/min

ICP-M S introduction water: $HNO_3$ (1 mM), 0.1 mL/min

Circulate the water flowing out from the first generation chamber 27 to the inlet of the first generation chamber 27

Introduce the concentrated water from the second generation chamber 28 into ICP-M S during analysis Applied voltage: 50 V (current value/approx. 2 mA to 5 mA)

<<First Electrodialyzer>>

Water supply to anode chamber: ultrapure water, 2 mL/min

Water supply to cathode chamber: $KNO_3$ (10 mM), 2 mL/min

Water supply to nitric acid generation chamber 16: ultrapure water, 0.1 mL/min Current value: approx. 0.23 mA <Elements to be Analyzed>

Na, Mg, Al, K, Ca, Cr, Mn, Fe, Co, Rb, Sr, Ni, Cu, Zn, Cd, Pb, Cs, Ba, and Bi

<Metal Concentration in Sample Water>

1 ng/L to 25 ng/L

Experimental Result

Figure 2:
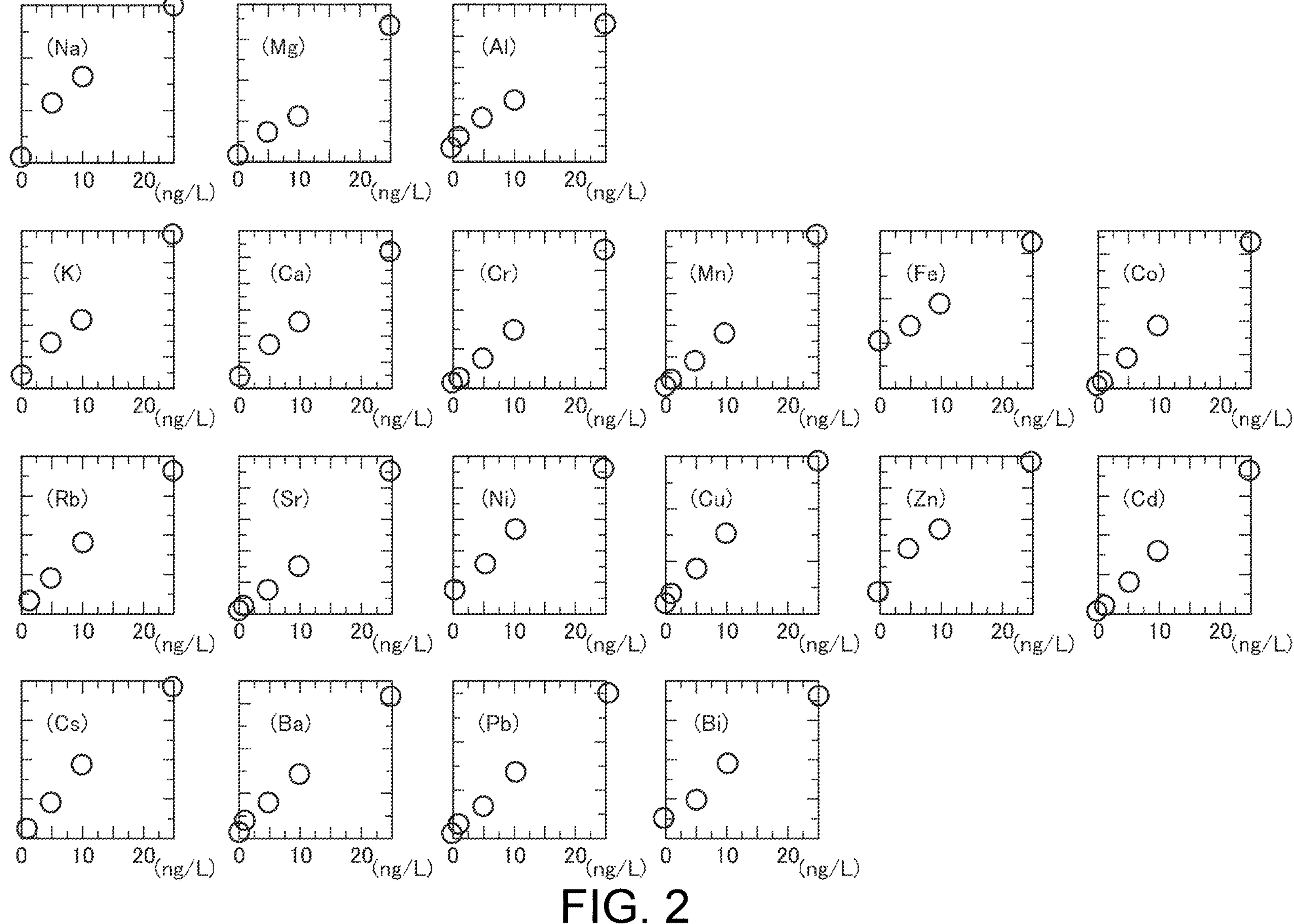
FIG. 2 includes graphs showing results of examples.

Evaluation results of 50-fold concentration of each of the above metals in the amount of 1 ng/L to 25 ng/L are shown in FIG. 2. In each graph of FIG. 2, the vertical axis indicates signal strength (cps) detected by ICP-MS, and the horizontal axis indicates the concentration of each metal ion. The types of the metal ions are described in the graphs. As shown in FIG. 2, extremely low levels of concentration of each metal ion were measured with high accuracy.

Although the invention has been described in detail using specific aspects, it will be apparent to those skilled in the art that various changes can be made without departing from the spirit and scope of the invention.

The present application is based on Japanese Patent Application No. 2021-158070 filed on Sep. 28, 2021, and is incorporated by reference in its entirety.

DESCRIPTION OF REFERENCE NUMERALS

10 first electrodialyzer
11, 21 anode
12, 22 cathode
13 bipolar membrane
14, 23, 25 anion exchange membrane
15, 26 anode chamber
16 nitric acid generation chamber
17, 29 cathode chamber
20 second electrodialyzer
24 dialysis membrane
27 first generation chamber
28 second generation chamber

The invention claimed is:

1. A method for analyzing ionic components in ultrapure water, in which sample ultrapure water is concentrated and analyzed by an analysis part, the method comprising:

concentrating the sample ultrapure water by an electrodialyzer, in which the electrodialyzer is a second electrodialyzer that comprises a first anion exchange membrane, a dialysis membrane, and a second anion exchange membrane arranged in this order between an anode and a cathode, and that comprises an anode chamber, a first generation chamber, a second generation chamber, and a cathode chamber arranged in this order from the anode to the cathode, wherein the method comprises:

passing sample ultrapure water through the first generation chamber;

passing a nitric acid aqueous solution through the anode chamber and the cathode chamber;

passing a high-purity nitric acid aqueous solution through the second generation chamber, the high-purity nitric acid aqueous solution being generated by transmitting $NO_3^-$ ions through an anion exchange membrane by a dialysis treatment and causing the $NO_3^-$ ions to move in ultrapure water; and analyzing concentrated water from the second generation chamber by the analysis part.

2. The method for analyzing ionic components in ultrapure water according to claim 1, wherein the high-purity nitric acid aqueous solution that is passed through the second generation chamber of the second electrodialyzer is generated by dialyzing a nitrate aqueous solution by a first electrodialyzer.

3. The method for analyzing ionic components in ultrapure water according to claim 2, in which the first electrodialyzer is an electrodialyzer that comprises a bipolar exchange membrane and an anion exchange membrane arranged in this order between an anode and a cathode, and that comprises an anode chamber, a nitric acid generation chamber, and a cathode chamber arranged in this order from the anode to the cathode, wherein the method comprises:

passing ultrapure water through the anode chamber and the nitric acid generation chamber;

passing the nitrate aqueous solution through the cathode chamber; and extracting the high-purity nitric acid aqueous solution from the nitric acid generation chamber.

4. The method for analyzing ionic components in ultrapure water according to claim 2, wherein the nitrate comprises potassium nitrate, sodium nitrate, or lithium nitrate.

5. A device for analyzing ionic components in ultrapure water, comprising:

an electrodialyzer, concentrating the sample ultrapure water; and an analysis part, measuring an ion concentration in concentrated water concentrated by the electrodialyzer, wherein the electrodialyzer is a second electrodialyzer that comprises a first anion exchange membrane, a dialysis membrane, and a second anion exchange membrane arranged in this order between an anode and a cathode, and that comprises an anode chamber, a first generation chamber, a second generation chamber, and a cathode chamber arranged in this order from the anode to the cathode, wherein sample ultrapure water is passed through the first generation chamber;

a nitric acid aqueous solution is passed through the anode chamber and the cathode chamber;

a high-purity nitric acid aqueous solution is passed through the second generation chamber, the high-purity nitric acid aqueous solution being generated by transmitting $NO_3^-$ ions through an anion exchange membrane by a dialysis treatment and causing the $NO_3^-$ ions to move in ultrapure water; and concentrated water from the second generation chamber is analyzed by the analysis part.

6. The device for analyzing ionic components in ultrapure water according to claim 5, comprising:

a first electrodialyzer for generating the high-purity nitric acid aqueous solution that is passed through the second generation chamber of the second electrodialyzer.

7. The device for analyzing ionic components in ultrapure water according to claim 6, wherein the first electrodialyzer is an electrodialyzer that comprises a bipolar exchange membrane and an anion exchange membrane arranged in this order between an anode and a cathode, and that comprises an anode chamber, a nitric acid generation chamber, and a cathode chamber arranged in this order from the anode to the cathode, wherein ultrapure water is passed through the anode chamber and the nitric acid generation chamber;

a nitrate aqueous solution is passed through the cathode chamber; and the high-purity nitric acid aqueous solution is extracted from the nitric acid generation chamber.

* * * * *